United States Patent [19]

Gristina

[11] 4,040,131
[45] Aug. 9, 1977

[54] TRISPHERICAL PROSTHETIC SHOULDER DEVICE

[75] Inventor: Anthony G. Gristina, Winston-Salem, N.C.

[73] Assignee: Howmedica, Inc., New York, N.Y.

[21] Appl. No.: 757,559

[22] Filed: Jan. 7, 1977

Related U.S. Application Data

[63] Continuation-in-part of Ser. No. 681,805, April 29, 1976, Pat. No. 4,003,095.

[51] Int. Cl.² .............................................. A61F 1/24
[52] U.S. Cl. .................................... 3/1.91; 128/92 C
[58] Field of Search ........................... 3/1, 1.9–1.913; 128/92 C, 92 CA

[56] References Cited

U.S. PATENT DOCUMENTS

| 133,620 | 12/1872 | Benedict | 403/122 X |
| 3,638,243 | 2/1972 | Campbell, Jr. et al. | 3/1.91 |
| 3,694,820 | 10/1972 | Scales et al. | 3/1.91 |
| 3,815,157 | 6/1974 | Skorecki et al. | 3/1.91 |
| 3,842,442 | 10/1974 | Kolbel | 3/1.91 |
| 3,869,730 | 3/1975 | Skobel | 3/1 |
| 3,889,299 | 6/1975 | Osborne et al. | 3/1.913 |
| 3,916,451 | 11/1975 | Buechel et al. | 3/1.91 |

FOREIGN PATENT DOCUMENTS

| 426,096 | 6/1967 | Switzerland | 3/1.912 |
| 1,362,187 | 7/1974 | United Kingdom | 3/1.91 |

*Primary Examiner*—Ronald L. Frinks
*Attorney, Agent, or Firm*—Connolly and Hutz

[57] ABSTRACT

Biocompatible metal balls are secured by affixation stems to the humerus and the scapular region of the shoulder. The balls are rotatably captured between a pair of cutout plastic hemispheres, which are secured to each other to form a spheroid by a metal shell. The prosthesis accordingly provides a wide range of articulation with substantially high stability.

6 Claims, 9 Drawing Figures

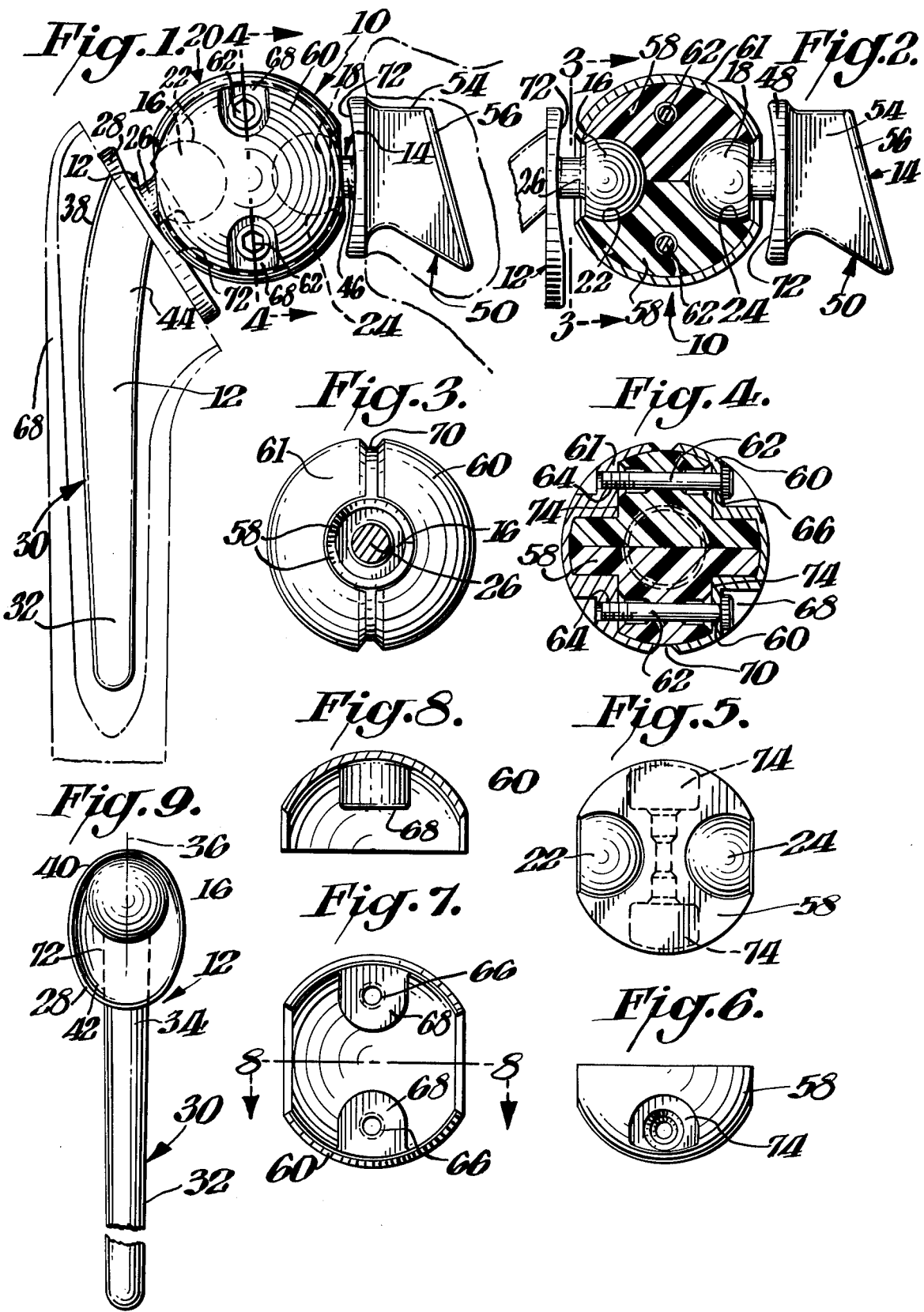

4,040,131

TRISPHERICAL PROSTHETIC SHOULDER DEVICE

CROSS REFERENCE TO RELATED APPLICATIONS

This application is a continuation-in-part of copending U.S. Pat. application Ser. No. 681,805, filed April 29, 1776, which issued as U.S. Pat. No. 4,003,095 on Jan. 18, 1977.

BACKGROUND OF THE INVENTION

Total replacement of the humeral shoulder joint requires a prosthesis with stability and range of motion comparable to the human shoulder. A device which highly satisfies these requirements is described in U.S. Pat. No. 4,003,095. An object of this invention is to provide an improved total replacement shoulder of the type described in U.S. Pat. No. 4,003,095, having more position retention of the component parts.

SUMMARY

In accordance with this invention the high density cutout plastic hemispheres of the type described in U.S. Pat. No. 4,003,095 are joined together about the heads of the ball by a pair of substantially hemispherical metal shells. The shells are secured together to provide a stable assembly which positively retains the balls captured within the plastic insert and shell. The flanges of the scapular and humeral components are concavely depressed and arranged at a distance relative to the necks and balls thereof to cause the outside of the shell to abut against the concave surfaces of the flanges to limit the meshing movement of the components whereby sharp contact between the edge of the shell and necks of the components is prevented.

BRIEF DESCRIPTION OF THE DRAWING

Novel features and advantages of the present invention will become apparent to one skilled in the art from a reading of the following detailed description in conjunction with the accompanying drawings wherein similar reference characters refer to similar parts and in which:

FIG. 1 is a view in elevation showing an embodiment of this invention installed between the human shoulder and upper arm;

FIG. 2 is a partial view of the prosthesis shown in FIG. 1 in an articulated position.

FIG. 3 is a cross-sectional view taken through FIG. 2 along the line 3—3;

FIG. 4 is a cross-sectional view taken through FIG. 1 along the line 4—4;

FIG. 5 is an exterior plan view of one of the hemispherical plastic inserts used in the embodiment shown in FIGS. 1-4, with the other insert being a mirror image thereof.

FIG. 6 is an external elevational view of the insert shown in FIG. 5;

FIG. 7 is an internal plan view of the threaded retaining shell used in the embodiment shown in FIGS. 1-4 with the unthreaded shell substantially being a mirror image thereof;

FIG. 8 is a cross-sectional view taken through FIG. 7 along the line 8—8; and

FIG. 9 is a front elevational view of the humeral component used in the embodiment shown in FIGS. 1-4.

DESCRIPTION OF THE PREFERRED EMBODIMENTS

In. FIG. 1 is shown trispherical prosthetic shoulder device 10 including a humeral component 12 and a scapular component 14 having respectively a humeral ball 16 of relatively small diameter, such as about ½ inch or 12.5 mm and a scapular ball 18 of about the same diameter. Humeral ball 16 and scapular ball 18 are rotatably captured by a central spheroidal component or insert 20 about 1 1/8 inches or 28.5 mm in diameter. Spherical sockets 22 and 24 in central component 20 rotatably capture slightly more than one half of the spherical heads of balls 16 and 18 to securely rotatably capture them. Humeral component 12 also includes a neck 26 connecting ball 16 to flange 28 of substantially elliptical or oval shape (shown in FIG. 9). Ball 16 and neck 26 are eccentrically disposed approximately at one of the foci of elliptical flange 28. Stem 30 is connected to the other side of flange 28 and its slightly tapered end 32 is disposed at an angle of approximately 30° relative to flange 28. Neck 26 and ball 16 are disposed substantially perpendicularly to the other side of flange 28. The attached end 34 of stem 30 is slightly radially curved in planes parallel to the main axis 36 of flange 28, and has its convex surface 38 substantially contiguous to the outer edge 40 of the nearer end of flange 28. The other end 42 of flange 28 extends outwardly a considerable distance from the concave surface 44 of curved stem portion 34.

Humeral component 12 and scapular component 14 are made of a biocompatible metal, such as, for example Vitallium. Vitallium is the trademark of Howmedica, Inc., for a special cobalt-chromium alloy developed and used for cast partial and full dentures and for internal applications by surgeons. Cobalt and chromium constitute over 90% of its composition. Vitallium is characterized by a specific gravity of 8.29; tensile strength, 95,000 lb.Sq.in. minimum; 2% offset yield strength, 65,000 lb./sq.in. minimum; reduction of area, 8% minimum; elongation, 8% minimum; and modulus of elasticity, 30,000,000–32,000,000 lb./sq.in. When polished, it is exceedingly smooth and permanently lustrous. Its outstanding qualities are clinical inertness in relation to living tissues and high degree of resistance to corrosion.

Scapular component 14 has a neck 46 joining ball 18 to substantially the center of elliptical flange 48, (as shown in FIG. 2) in a substantially perpendicular disposition. T-shaped affixation stem 50 is joined to the other side of flange 48. Stem 50 includes a substantially narrow web 54 joining elongated base 56 to flange 48. Web 54 is longer at one end than the other and thus disposes base 56 at an acute angle relative to flange 48, such as approximately 15°. Scapular stem 50 and humeral stem 30 are both cemented in place by a suitable bone cement, such as methyl methacrylate.

Central component 20 includes a pair of plastic cutout hemispheres of biocompatible plastic 58, shown in FIGS. 2, 3, and 4 sharing spherical sockets 22 and 24 of a slightly greater than radial depth for capturing balls 16 and 18. Hemispheres 58 are, for example, made of high density or ultra-high density polyethylene. They are joined securely together about balls 16 and 18 by a pair of hemispherical shells 60, 61 and hexagonal headed cap screws 62 engaged in threaded sockets 64 in shell 61 and passing through smooth socket 66 in shell 60. Shells 60 and 61 and screws 62 are also made of Vitallium, for example. Sockets 64 and 66 and the heads of cap screws 62 are secured within indentations 69 in shells 60 and 61. Indentations 69 in shells 60 and 61 are received in mating indentations 74 in hemispherical inserts 58.

FIGS. 1 and 2 show various articulated positions of shoulder prosthesis 10. FIG. 1, humeral component 12 and human arm 68 are disposed in a substantially downwardly extending vertical position with the inward motion of humeral component 12 arrested by contact of neck 26 on the lower edge of socket 22.

FIG. 2 shows a somewhat raised position of prosthesis 10 in which ball 16 of central component 20 has rotated upwardly within socket 22 to approximately 30° from the position shown in FIG. 1.

FIG. 3 shows narrow space 70 between shells 60 and 61 when they are secured together. This space insures firm engagement of plastic inserts 58 together about balls 16 and 18. Due to overlap or extension of plastic shown in FIG. 1 beyond equator of spherical heads, there is provided total retention of all of the ball components within plastic inserts 58. Also, total capture of parts 10 is provided since the opening in the metal shell is less than the diameter of the spherical heads.

At extreme end of motion contact occurs between the outer surface 72 of the flanges 28 and 48 and the outside surfaces of the metal shells 60 and 61. This distributes the load over a greater area which reduces impact stresses. Many current designs allow contact of the neck with the thin edge of the mating part. This arrangement can lead to deformation of the contacting surfaces due to the high bearing stresses which can occur.

During end of allowable range of motion the parts cannot "cam-out". Either implantable component will rotate around instant center producing rotational vector which is directed into the plastic and surrounding metal shell. This means that in order for dislocation to occur the spherical head must completely deform plastic and product local yielding of the shell —which is a very unlikely possibility.

I claim:

1. A trispherical prosthetic shoulder device comprising a relatively small ball-headed humeral component of a biocompatible metal, a humeral stem on the ball-headed humeral component for affixing it to the intermedullary canal of the humerus, a humeral flange separating the ball-headed component from the stem, a ball-headed scapular component of a biocompatible metal, a scapular stem on the scapular component for attaching it to the scapular region of the shoulder, a scapular flange separating the scapular ball from the scapular stem, a spheroidal ball-capturing member having a pair of spherical sockets disposed substantially 180° from each other, the ball-capturing member comprising a pair of biocompatible cutout plastic hemispheres sharing the sockets between them, clamping means joining the hemispheres together whereby the ball heads are rotatably trapped in the sockets to provide a substantially stable shoulder prosthesis with a substantially wide range of movement, and the clamping means comprising a pair of metal shells substantially surrounding and enclosing the hemispheres and fastening means joining the metal shells together.

2. A trispherical prosthetic shoulder device as set forth in claim 1 wherein the metal shells incorporate peripheries and indentations therein, and the indentations having sockets for receiving fastening devices within the peripheries.

3. A trispherical prosthetic shoulder device as set forth in claim 2 wherein the spheroidal ball capturing member includes further indentations, and the further indentations are innerlocked with the indentations in the pair of metal shells to positively lock the spheriodal ball capturing member and shells together.

4. A trispherical prosthetic shoulder device as set forth in claim 3 wherein the spheroidal ball capturing members and the shells have joining areas, and the joining areas are offset from each other.

5. A trispherical prosthetic shoulder device as set forth in claim 1 wherein the fastening means comprise sockets in the shells and cap screws inserted in the sockets.

6. A trispherical prosthetic shoulder device as set forth in claim 1 wherein the humeral and scapular components include flanges, the humeral and scapular components having balls being connected to the flanges by necks, and the surfaces of the flanges dipsosed adjacent the balls being concavely shaped, constructed and arranged so that the outside of the shells contact the concave surfaces in the shells to limit the relative motion in the components against each other.

* * * * *